United States Patent [19]

Grüning et al.

[11] Patent Number: 5,792,737

[45] Date of Patent: Aug. 11, 1998

[54] MILD, AQUEOUS, SURFACTANT PREPARATION FOR COSMETIC PURPOSES AND AS DETERGENT

[75] Inventors: Burghard Grüning; Christian Weitemeyer, both of Essen, Germany

[73] Assignee: Th. Goldschmidt AG, Essen, Germany

[21] Appl. No.: 843,552

[22] Filed: Apr. 18, 1997

Related U.S. Application Data

[63] Continuation-in-part of Ser. No. 549,905, Oct. 30, 1995.

[30] Foreign Application Priority Data

Nov. 7, 1994 [DE] Germany .................. 44 39 642.2

[51] Int. Cl.$^6$ ................................................. C11D 1/90
[52] U.S. Cl. ..................... 510/126; 510/130; 510/137; 510/499
[58] Field of Search ....................... 510/126, 130, 510/137, 499; 554/35

[56] References Cited

FOREIGN PATENT DOCUMENTS

| 500946 | 9/1992 | European Pat. Off. . |
| 353580 | 9/1993 | European Pat. Off. . |
| 3011549 | 10/1981 | Germany . |
| 1152199 | 6/1989 | Japan . |

OTHER PUBLICATIONS

Pape, W.J.W.; Hoppe, U., Standardization of an in vitro Red Blood Cell Test for Evaluating the Acute Cytotoxic Potential of Tensides, 40(I), Nr. 4, 498–502 (1990).

Dr. Kunzmann, Th.; and Dr. Kantrowitz, H., Seifen–Ole–Fette–Wachse, Kosmetik—Die Chem.-Techn.Industrie, 93.Jahrgang—Nr. 15, 521(1967).

*Primary Examiner*—Paul Lieberman
*Assistant Examiner*—John R. Hardee
*Attorney, Agent, or Firm*—Anderson, Kill & Olick, P.C.

[57] ABSTRACT

The invention relates to mild, aqueous, surfactant preparations for cosmetic purposes and as detergents. These preparations contain, as surfactants, betaines of the general formula

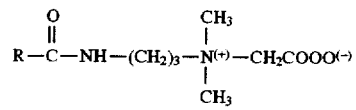

in which R is an alkyl group with 7 to 21 carbon atoms, 20 to 100% by weight of the betaines used as R group having an alkyl group with 7 to 9 carbon atoms, in an amount of 1.0 to 40% by weight of the preparation used. These preparations are distinguished by their exceptionally mild and low irritating properties when used, for example, in face lotions, shampoos or lotions.

5 Claims, No Drawings

MILD, AQUEOUS, SURFACTANT PREPARATION FOR COSMETIC PURPOSES AND AS DETERGENT

This is a continuation-in-part application of Ser. No. 08/549,905, filed Oct. 30, 1995.

FIELD OF THE INVENTION

The invention relates to mild, aqueous, surfactant preparations for cosmetic purpose and detergents.

BACKGROUND INFORMATION AND PRIOR ART

Betaines and, particularly amidopropyl betaines, are used as amphoteric surfactants especially for hair preparations and in cleansing agent preparations for the skin, such as shampoos, foam gels and shower gels, which are gentle on the skin, and for intimate and body cosmetics. In addition to other desirable properties, they improve the dermatological properties of anionic and nonionic surfactants and cause the skin to feel pleasant. Furthermore, the betaines can also be used to advantage in cleansing agents, such as dish rinsing aids and detergents for delicate fabrics.

As betaines of the state of the art, particularly fatty acid amidopropyl betaines are used, the fatty acid groups of which generally have 8 to 18 or 12 to 18 carbon atoms in the mixture. The amidopropyl betaines of coconut oil fatty acids, with the following composition, has proven to be particularly effective:

Fatty acid group with 8 carbon atoms ca. 7%
Fatty acid group with 10 carbon atoms ca. 6%
Fatty acid group with 12 carbon atoms ca. 49%
Fatty acid group with 14 carbon atoms ca. 19%
Fatty acid group with 16 carbon atoms ca. 9%
Fatty acid group with 18 carbon atoms ca. 10%

Even though mild surfactant formulations can be prepared with amidopropyl betaines of coconut oil fatty acids, conventional, commercial, aqueous solutions of the betaine or their dilutions with water have a distinct irritant potential, which can be determined in tests on the skin and mucous membranes, and also by modern in vitro test methods for determining the irritant effect, such as the erythrocyte test.

Aside from this, the constant demands of the consumer for milder cosmetic preparations and cleansing agents make it necessary to have particularly mild surfactants available.

It is therefore an object of the invention to find exceptionally mild, low-irritant preparations, which satisfy the demands of high skin compatibility.

OBJECT OF THE INVENTION

An object of the present invention is aqueous, surfactant preparation for cosmetic purpose and detergents.

SUMMARY OF THE INVENTION

Surprisingly, surfactant preparations were found, which contain, as surfactants, betaines of the general formula

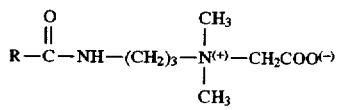

in which R is an alkyl group with 7 to 21 carbon atoms, 20 to 100% by weight of the betaines used as R group being an alkyl group with 7 to 9 carbon atoms, in an amount of 1.0 to 40% by weight of the preparation used.

These inventive preparations are appreciably milder and less irritant than those of the state of the art and lead to only slight or practically no irritations when used, for example, for face lotions, shampoos or lotions.

It was surprising that especially betaines with a relatively short-chain fatty acid group show these particularly mild properties, because increased irritating properties were assigned in the technical literature especially to those surfactants, which are distinguished by short-chain fatty acid groups.

For example, it can be inferred from the publication Seifen-Öle-Fette-Wachse, vol. 93, No. 15/1967 of Jul. 19, 1967, on page 521 that the dermatological properties of surfactants with shorter alkyl chains are less satisfactory. It is therefore recommended that surfactants with alkyl chain 12 to 14 or 12 to 18 carbon atoms be used in the cosmetic sector.

In the same sense, the German patent 30 11 549 teaches that alkyl ether sulfates, which have a larger proportion of alkyl groups with 14 carbon atoms, produce milder formulations than do alkyl ether sulfates, which have a larger proportion of groups with 12 carbon atoms and a smaller proportion of groups with 14 carbon atoms.

It is advisable that the inventive preparations contain these betaines in an amount of 1.5 to 20% by weight, based on the preparation.

It is of advantage if 40 to 100% by weight of these betaines have an alkyl group with 7 to 9 carbon atoms.

Particularly preferred are preparations, in which more than 90% by weight of the betaines used have an alkyl group with 7 to 9 carbon atoms.

The inventive preparations may contain anionic surfactants. As suitable anionic surfactants, particularly alkyl ether sulfate and furthermore monoglyceride sulfates, alkyl ether carboxylic acids and their alkali salts may be mentioned as mild, skin-compatible detergents.

Long-chain acyl sarcosinates or their alkali salts, such as sodium lauroyl sarcosinate, are a further preferred class of anionic surfactants.

Other anionic surfactants suitable within the scope of the invention are alpha-olefin sulfonates, alkyl sulfates and their salts and, in particular, alkali salts of half esters of sulfosuccinic acid.

The inventive preparations can furthermore also contain nonionic surfactants. A preferred nonionic surfactant belongs to the class of alkyl polyglucosides of the general formula

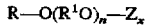

wherein R is an alkyl group with 8 to 18 carbon atoms, $R^1$ is an ethylene or propylene group, Z is a saccharide group with 5 to 6 carbon atoms, n is a number from 0 to 10 and x is a number between 1 and 5.

Although alkyl polyglucosides of the above-named general formula are preferred as nonionic surfactants in the inventive compositions, it is also possible to use other nonionic surfactants instead of the ones mentioned or preferably a mixture thereof. Such other nonionic surfactants are, for example, fatty acid esters of multihydric alcohols, such as glycerin, fatty acid polyglycol esters, fatty alcohol ethoxylates and mixed products of ethylene oxide and propylene oxide. Other nonionic surfactant components may be amine oxides and fatty acid monoalkanolamides and dialkanolamides.

The inventive, mild, aqueous, surfactant preparations may contain all materials normally used in such agents.

Named as such are stabilizers, perfume oils, thickeners, which can originate from the group of associative thickeners or the group of polymeric thickeners, such as polyacrylic acid and its derivatives, cellulose derivatives and alginates, dyes, conditioning and cosmetic components, such as cationic, amphoteric polymers, lanolin derivatives, cholesterol, pentothenic acid, polydimethylsiloxanes or their derivatives, preservatives, with the exception of hinokitiol, etc.

A hypoirritant surfactant preparation, similar to the one herein disclosed, was taught by Hayakawa, EP 500,946. However, Hayakawa requires the use of hinokitoil or a salt thereof, as a necessary ingredient. The inventor of the herein disclosed compound has found that a less irritating compound can be made if hinokitoil is excluded. Further, this less irritating compound is better suited for some of the disclosed applications such as cosmetic preparations.

The inventive products are prepared by stirring the individual components together in water. Mixtures of different components can also be used.

The surprisingly mild action of the betaines in inventive preparations, the fatty acid groups of which are derived to the extent of more than 20% from $C_8/C_{10}$ fatty acids, is shown by means of the following comparison examples. The percentages given are percentages by weight. It is understood that the following examples are provided by way of illustration and not by way of limitation.

EXAMPLE 1

The physiological compatibility of fatty acid amidopropyl betaines, derived from fatty acids of different chain lengths, is investigated with the help of an in vitro method, the erythrocyte test (RBC). The RBC test is described by J. W. Pape and U. Hoppe in the journal, Arzneim.-Forsch./Drug Res. 40, 498, (1990) and is carried out as described there.

The destruction of blood cells by lysis and the denaturing of the hemoglobin released were measured for characterizing the typical irritative interactions of surfactants with whole cell structure. The result is expressed as L/D, the quotient of lysis (L) and denaturing (D). The smaller the L/D value, the more irritating is the substance or formulation.

The results are summarized in Table 1. The following abbreviated formulation is used for the fatty acid amidopropyl betaines used:

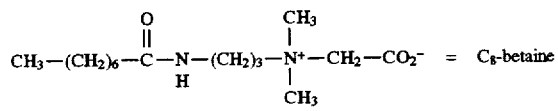
= $C_8$-betaine

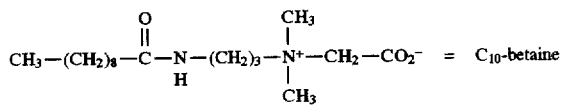
= $C_{10}$-betaine

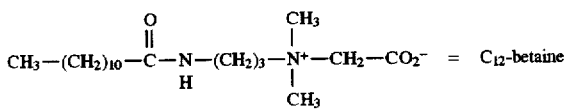
= $C_{12}$-betaine

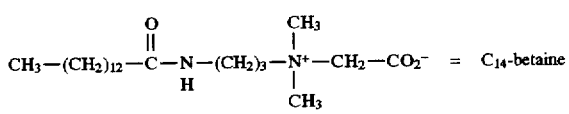
= $C_{14}$-betaine

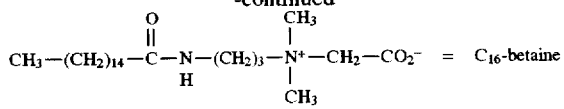
= $C_{16}$-betaine

TABLE 1

| Betaine | L | D | L/D |
|---|---|---|---|
| $C_8$-Betaine | no hemolysis | | >>100 |
| $C_{10}$-Betaine | no hemolysis | | >>100 |
| $C_{12}$-Betaine | 151 | 17 | 8.9 |
| $C_{14}$-Betaine | 13 | 9.2 | 1.4 |
| $C_{16}$-Betaine | 4.4 | 4.4 | 1.0 |

The Table shows that the irritating action of the betaines on the skin and mucous membrane increases with the length of the alkyl chain. The short-chain fatty acid amidopropyl betaines, which are derived from caprylic and capric acids, exert practically no irritating effect.

EXAMPLE 2

Mild surfactant formulations are produced from $C_8/C_{10}$ betaine and coconut oil fatty acid amidopropyl betaine (coconut oil betaine) and differ with respect to their $C_8/C_{10}$ betaine and coconut oil betaine content. The $C_8/C_{10}$ betaine is composed of equal parts of $C_8$ and $C_{10}$ betaines. The coconut oil betaine is characterized by the following distribution of fatty acids:

| | |
|---|---|
| $C_8$-betaine | 7.2% |
| $C_{10}$-betaine | 5.8% |
| $C_{12}$-betaine | 49.0% |
| $C_{14}$-betaine | 18.6% |
| $C_{16}$-betaine | 9.1% |
| $C_{18}$-betaine | 10.3% |

The composition of the formulations and their irritant effect, as determined by the RBC test, are listed in Table 2.

TABLE 2

| Formula | A | B | C | D | E |
|---|---|---|---|---|---|
| $C_8/C_{10}$-Betaine (%) | 15 | — | 5 | 7.5 | 10 |
| Coconut Oil Betaine (%) | — | 15 | 10 | 7.5 | 5 |
| Proportion of $C_8/C_{10}$ in betaine (%) | 100 | 13 | 42 | 57 | 72 |
| L | — | 24 | 37 | 51 | 75 |
| D | — | 8.4 | 3.2 | 2.2 | 2.2 |
| L/D | >>100 | 2.9 | 11 | 23 | 34 |

The results show that the irritating effect of the betaine decreases clearly and its compatibility increases clearly as the content of $C_8/C_{10}$ portions increases.

EXAMPLE 3

Mild surfactant formulations are produced from $C_8/C_{10}$ betaine and the surfactants described below. These formulations are compared with similar formulations based on $C_{12}$ betaine or coconut oil fatty acid amidopropyl betaine. In each case, the formulations contain 10% of active betaine substance and 5% of the active second surfactant substance. Aside from water, the formulations do not contain any other components.

As in Example 2, the $C_8/C_{10}$ is composed of equal parts of $C_8$ betaine and $C_{10}$ betaine. The composition of the coconut oil fatty acid amidopropyl betaine is identical with that of the product used in Example 2.

The surfactants used in addition to the betaines are:

the disodium salt of lauryl sulfosuccinate (LSSDNa), commercially obtainable under the name of TEGO SULFOSUCCINATE F 30 (Th. Goldschmidt AG);

sodium lauroyl sarcosinate (NaLSC), commercially obtainable under the name of Hamposyl L 30 (Grace); and lauroyl polyglucoside (APG) commercially obtainable under the name of Plantaren 1200 (Henkel).

The composition of the formulations and their irritant action, determined by the RBC test, are listed in Table 3.

TABLE 3

|  | LSSDNa | | | NaLSC | | | APG | | |
| --- | --- | --- | --- | --- | --- | --- | --- | --- | --- |
|  | L | D | L/D | L | D | L/D | L | D | L/D |
| $C_8/C_{10}$-betaine | *) | 22 | >100 | 563 | 20 | 28 | no hem | | >>100 |
| $C_{12}$-betaine | 49 | 13 | 3.8 | 84 | 18 | 4.7 | 81 | <1 | >100 |
| Coconut oil betaine | 22 | 4.6 | 4.8 | 36 | 12 | 3.0 | 46 | <1 | >100 | hem = hemolysis, *) = no complete hemolysis

The results make it clear that surfactant formulations, which are based on $C_8/C_{10}$ betaine, have a distinctly lower irritant effect than do those, which are based on $C_{12}$ betaine or coconut oil betaine.

EXAMPLE 4

Mild surfactant formulations are produced from $C_8/C_{10}$ betaine and three other surfactants, which are described in Example 3. The formulations contain 5 to 10% $C_8/C_{10}$ betaine and 10 to 5% of the disodium salt of lauryl sulfosuccinate (LSSDNa), sodium lauroyl sarcosinate (NaLSC) or sodium lauryl polyglucoside (APG). Those which contain 10% $C_8/C_{10}$ betaine, are identical with the ones described in Example 3. The formulations are tested with the RBC test for their physiological compatibility. The results are shown in Table 4.

TABLE 4

| Formulation | F | G | H | I | K | L | N | N | O |
| --- | --- | --- | --- | --- | --- | --- | --- | --- | --- |
| $C_8/C_{10}$ betaine(%) | 10 | 7.5 | 5 | 10 | 7.5 | 5 | 10 | 7.5 | 5 |
| LSSDNa (%) | 5 | 7.5 | 10 | — | — | — | — | — | — |
| NaLSC (%) | — | — | — | 5 | 7.5 | 10 | — | — | — |
| APG (%) | — | — | — | — | — | — | — | 7.5 | 10 |
| L | * | * | * | 563 | 409 | 307 | ** | ** | ** |
| D | 22 | 31 | 42 | 20 | 37 | 55 | — | — | — |
| L/D | >100 | >100 | >100 | 28.2 | 11.1 | 5.6 | >>100 | >>100 | >>100 |

* = no complete hemolysis
** = no hemolysis

All formulations, shown in Table 4, are very mild. Moreover, it becomes clear that the formulations, which contain the greatest proportion of $C_8/C_{10}$, are the mildest. For formulations F to H, this is evident from the denaturation values (D) and for formulations I to L, this is evident from the lysis values (L) as well as from, the denaturation values.

EXAMPLE 5

| Formulations Face Lotions | |
| --- | --- |
| Water | 85.5% |
| Ethanol | 5.0% |
| $C_8/C_{10}$ Betaine[1] | 3.7% |
| Moisturizer[2] | 2.0% |
| Hamamelis Extract[3] | 2.0% |
| Glycerin-(6)-polyglycol ether caprylate/caprate[4] | 1.5% |
| Allantoin | 0.3% |

[1] 50% aqueous solution
[2] CTFA name: sodium lactate (and) sodium PCA (and) glycine (and) fructose (and) urea (and) niacinamide (and) inotisotol (and) sodium benzoate (and) lactic acid, commercially obtainable under the name of LACTIL (Th. Goldschmidt, AG)
[3] Commercially obtainable under the name of Extrapon Hamamelis (Dragoco)
[4] CTFA name: PEG-6 caprylic/capric glycerides, commercially obtainable under the name of TEGOSOFT GMC6 (Th. Goldschmidt AG)

| Conditioning Shampoo | |
| --- | --- |
| Water | 43.1% |
| Sodium lauryl ether sulfate (28% aqueous solution)[5] | 32.0% |
| $C_8/C_{10}$ betaine[1] | 22.0% |
| Polyacrylate-based thickener[6] | 2.0% |
| Cationic guar[7] | 0.5% |
| Cationic siloxane (50% solution in propylene glycol)[8] | 0.4% |
| Perfume | 0.3% |

[5] CTFA name: Sodium laureth sulfate, commercially obtainable under the name of Texapon N 25 (Henkel)
[6] CTFA name: Acrylates steareth-50 acrylate copolymer (and) laureth-3 (and) propylene glycol, commercially obtainable under the name of ANTIL 208 (Th. Goldschmidt AG)
[7] CTFA name: Guar hydroxypropyl trimonium chloride, commercially obtainable under the name of Cosmedia Guar C261 (Henkel)
[8] CTFA name: Quaternium 80, commercially obtainable under the name of ABIL Quat 3272 (Th. Goldschmidt AG)

| Shower Gel | |
| --- | --- |
| Water | 40.0% |
| Disodium lauryl ether sulfosuccinate[9] | 17.3% |

| Shower Gel | |
|---|---|
| $C_8C_{10}$ betaine[1] | 17.0% |
| Lauryl polyglucoside[10] | 14.0% |
| Glycerin-(7)-polyglycol ether coconut oil fatty acid ester[11] | 5.0% |
| Polyacrylate-based thickener[6] | 4.0% |
| NaCl | 2.5% |
| Perfume | 0.2% |

[9]CTFA name: Disodium laurethsulfosuccinate, commercially obtainable under the name of TEGO SULFOSUCCINATE F 30 (Th. Goldschmidt)
[10]CTFA name: Lauryl polyglucose, commercially obtainable under the name of Plantaren 1200 (Henkel)
[11]CTFA name: PEG-7 glyceryl cocoate, commercially obtainable under the name of TEGOSOFT GC (Th. Goldschmidt AG)

| Baby Shampoo | |
|---|---|
| Water | 69.5% |
| Sodium lauryl ether sulfate (28% aqueous solution)[5] | 15.0% |
| Coconut oil fatty acid amidopropyl betaine[12] | 6.0% |
| Oleic acid/coconut oil fatty acid ester of glycerin-(18)-polyglycol ether[13] | 4.0% |
| Tallow fatty acid esters of glycerin (30)-polyglycol ether[14] | 3.0% |
| C8/C10 betaine[1] | 1.5% |
| NaCl | 0.7% |
| Perfume | 0.3% |

[12]CTFA name: Cocamidopropyl betaine, commercially obtainable under the name of Tego Betaine F 50 (Th. Goldschmidt AG).
[13]CTFA name: PEG-18 glyceryl oleate/cocoate, commercially obtainable under the name of ANTIL 171 (Th. Goldschmidt AG).
[14]CTFA name: PEG-30 glyceryl stearate, commercially obtainable under the name of TAGAT S (Th. Goldschmidt AG)

What is claimed is:

1. An aqueous, surfactant preparation for cosmetic purposes and detergents, comprising as a surfactant, betaines of a general formula

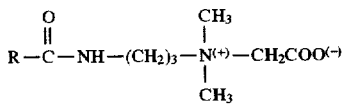

in which R is an alkyl group with 7 to 21 carbon atoms, 20 to 100% by weight of the betaines used having R with an alkyl group with 7 to 9 carbon atoms, in an amount of 1.0 to 40% by weight of the preparation, wherein hinokitiol is not an ingredient.

2. The preparation of claim 1, wherein the betaine is present in an amount of 1.5 to 20% by weight, based on the preparation.

3. The preparation of claims 1 or 2, wherein 40 to 100% by weight of the betaines used have an alkyl group with 7 to 9 carbon atoms as R group.

4. The preparation of claims 1 or 2, wherein more than 90% by weight of the betaines used have an alkyl group with 7 to 9 carbon atoms as R group.

5. The preparation of claims 1 or 2, further comprising anionic, nonionic surfactants or both in an amount of 1.0 to 40% by weight based on the preparation, with the proviso that the total surfactant content does not exceed 60% by weight.

* * * * *